(12) United States Patent
Guillama et al.

(10) Patent No.: US 9,370,689 B2
(45) Date of Patent: Jun. 21, 2016

(54) SYSTEM AND METHODS FOR PROVIDING DYNAMIC INTEGRATED WELLNESS ASSESSMENT

(71) Applicants: SynaBee, Inc., Wellington, FL (US); The Quantum Group, Wellington, FL (US)

(72) Inventors: Noel J. Guillama, Wellington, FL (US); Chester Heath, Boca Raton, FL (US)

(73) Assignee: THE QUANTUM GROUP, INC., Lake Worth, FL (US)

( * ) Notice: Subject to any disclaimer, the term of this patent is extended or adjusted under 35 U.S.C. 154(b) by 481 days.

(21) Appl. No.: 13/736,145

(22) Filed: Jan. 8, 2013

(65) Prior Publication Data
US 2013/0122476 A1   May 16, 2013

Related U.S. Application Data

(63) Continuation-in-part of application No. 12/349,714, filed on Jan. 7, 2009, now Pat. No. 8,352,408, and a continuation-in-part of application No. 13/302,557, filed on Nov. 22, 2011, now Pat. No. 8,823,500, which
(Continued)

(51) Int. Cl.
| | |
|---|---|
| *A63B 24/00* | (2006.01) |
| *G06N 99/00* | (2010.01) |
| *G06F 19/00* | (2011.01) |
| *G06Q 10/06* | (2012.01) |

(Continued)

(52) U.S. Cl.
CPC ............ *A63B 24/00* (2013.01); *G06F 19/3431* (2013.01); *G06N 99/005* (2013.01); *G06Q 10/067* (2013.01); *G06Q 10/107* (2013.01); *G06Q 50/22* (2013.01); *G06F 19/3437* (2013.01)

(58) Field of Classification Search
None
See application file for complete search history.

(56) References Cited

U.S. PATENT DOCUMENTS

| | | |
|---|---|---|
| 4,617,557 A | 10/1986 | Gordon |
| 5,412,372 A | 5/1995 | Parkhurst et al. |

(Continued)

FOREIGN PATENT DOCUMENTS

WO   0017799   3/2000

OTHER PUBLICATIONS

Jancey, J.M. et al. "A Physical Activity Program to Mobilize Older People: A Practical and Sustainable Approach." The Gerontologist, vol. 48, No. 2, 2008. pp. 251-257.*
(Continued)

*Primary Examiner* — Stanley K Hill
*Assistant Examiner* — Benjamin Buss
(74) *Attorney, Agent, or Firm* — POLSINELLI PC

(57) ABSTRACT

Systems and methods for generating and using measurable indexes for providing a total wellness assessment of an individual are provided. A method includes computing an overall health score corresponding to the individual based on a plurality of weighting factors, the weighting factors based at least on health conditions associated with the individual. The method also includes determining a set of recommended changes for the individual based on the overall health score and generating an episodic plan for the individual, the episodic plan comprising a series of episodes for the individual that when completed will result in the individual having implemented the set of recommended changes. The method further includes generating a series of prompts for the individual, the series of prompts selected to guide the individual through the episodic plan.

20 Claims, 7 Drawing Sheets

Related U.S. Application Data is a continuation-in-part of application No. 12/470,550, filed on May 22, 2009, now Pat. No. 8,154,390, application No. 13/736,145, which is a continuation-in-part of application No. PCT/US2012/052404, filed on Aug. 25, 2012.

(60) Provisional application No. 61/019,524, filed on Jan. 7, 2008, provisional application No. 61/527,287, filed on Aug. 25, 2011.

(51) Int. Cl.
*G06Q 10/10* (2012.01)
*G06Q 50/22* (2012.01)

(56) References Cited

U.S. PATENT DOCUMENTS

| | | | |
|---|---|---|---|
| 5,937,387 A | 8/1999 | Summerell et al. | |
| 6,380,858 B1 | 4/2002 | Yarin et al. | |
| 6,670,885 B2 | 12/2003 | Kosaka | |
| 6,973,371 B1 | 12/2005 | Benouali | |
| 7,230,521 B2 | 6/2007 | Terenna | |
| 7,366,675 B1 | 4/2008 | Walker et al. | |
| 7,755,478 B2 | 7/2010 | Niemiec et al. | |
| 7,928,835 B1 | 4/2011 | Jovanov et al. | |
| 7,956,727 B2 | 6/2011 | Loncar et al. | |
| 2002/0072932 A1* | 6/2002 | Swamy | G06Q 30/02 600/300 |
| 2002/0170193 A1* | 11/2002 | Townsend | A61B 5/1116 33/512 |
| 2003/0135391 A1* | 7/2003 | Edmundson et al. | 705/2 |
| 2005/0234742 A1* | 10/2005 | Hodgdon | 705/2 |
| 2006/0111944 A1 | 5/2006 | Sirmans et al. | |
| 2006/0129427 A1 | 6/2006 | Wennberg | |
| 2006/0287883 A1* | 12/2006 | Turgiss et al. | 705/2 |
| 2007/0016443 A1* | 1/2007 | Wachman | G06Q 50/22 600/300 |
| 2008/0046291 A1* | 2/2008 | Huang | G06F 19/3418 600/301 |
| 2008/0091463 A1* | 4/2008 | Shakamuri | G06F 19/3431 705/2 |
| 2008/0098313 A1 | 4/2008 | Pollack | |
| 2008/0102856 A1 | 5/2008 | Fortescue et al. | |
| 2008/0126124 A1* | 5/2008 | Schechter | 705/2 |
| 2008/0146334 A1* | 6/2008 | Kil | G06F 19/345 463/36 |
| 2008/0147441 A1* | 6/2008 | Kil | G06F 19/345 705/2 |
| 2008/0162496 A1* | 7/2008 | Postrel | G06Q 10/10 707/999.01 |
| 2008/0177567 A1* | 7/2008 | Friedlander | G06Q 40/08 705/2 |
| 2008/0188261 A1 | 8/2008 | Arnone | |
| 2008/0215623 A1 | 9/2008 | Ramer et al. | |
| 2008/0255873 A1* | 10/2008 | Berkley | 705/2 |
| 2008/0300916 A1* | 12/2008 | Parkinson et al. | 705/2 |
| 2009/0076903 A1* | 3/2009 | Schwarzberg | G06F 19/3475 705/14.19 |
| 2009/0132284 A1* | 5/2009 | Fey et al. | 705/3 |
| 2009/0215469 A1 | 8/2009 | Fisher et al. | |
| 2011/0071851 A1* | 3/2011 | Alden | G06F 19/327 706/47 |
| 2011/0145747 A1* | 6/2011 | Wong | A61B 5/0002 715/771 |
| 2011/0184247 A1* | 7/2011 | Contant et al. | 600/300 |
| 2012/0010867 A1* | 1/2012 | Eder | G06N 5/022 703/13 |
| 2012/0072233 A1* | 3/2012 | Hanlon | G06F 19/3475 705/2 |
| 2012/0130198 A1* | 5/2012 | Beaul | G06F 19/3431 600/300 |
| 2012/0191469 A1* | 7/2012 | Akradi | G06F 19/363 705/2 |
| 2012/0296455 A1* | 11/2012 | Ohnemus | G06F 19/3481 700/91 |
| 2012/0310661 A1* | 12/2012 | Greene | 705/2 |
| 2013/0117040 A1* | 5/2013 | James | G06Q 50/22 705/2 |
| 2013/0174073 A1* | 7/2013 | Ash | G06F 3/048 715/771 |
| 2013/0211858 A1* | 8/2013 | Ohnemus | G06F 19/322 705/3 |
| 2014/0172437 A1* | 6/2014 | Deng | G06F 19/3437 705/2 |
| 2014/0250043 A1* | 9/2014 | Malinsky et al. | 706/46 |
| 2014/0372133 A1* | 12/2014 | Austrum et al. | 705/2 |

OTHER PUBLICATIONS

International Search Report and the Written Opinion of the ISA issued in Appln No. PCT/US2012/52404 on Nov. 6, 2012. (14 pages).
Mehrotra et al., *Elements of artificial neural networks*, 1997, MIT press.
Non Final Office Action (USPTO) mailed on Dec. 15, 2011 in U.S. Appl. No. 12/349,714. (25 pages).
Non Final Office Action (USPTO) mailed on Jul. 15, 2011 in U.S. Appl. No. 12/470,550. (13 pages).

* cited by examiner

600

SYSTEM AND METHODS FOR PROVIDING DYNAMIC INTEGRATED WELLNESS ASSESSMENT

CROSS-REFERENCE TO RELATED APPLICATIONS

This application claims the benefit of U.S. patent application Ser. No. 12/349,714, filed Jan. 7, 2009, which claims priority to U.S. Provisional Patent Application No. 61/019,524, filed Jan. 7, 2008. This application also claims the benefit of U.S. patent application Ser. No. 13/302,557, filed Nov. 22, 2011, which claims priority to U.S. patent application Ser. No. 12/470,550, filed May 22, 2009. This application further claims priority to International Patent Application No. PCT/US12/52404, filed Aug. 25, 2012, which claims priority to U.S. Provisional Patent Application No. 61/527,287, filed Aug. 25, 2011. The contents of each of the foregoing are herein incorporated by reference in their entirety.

FIELD OF THE INVENTION

The present invention is related to the fields of data analysis and processing, and more particularly, to analyzing and processing data derived from disparate sources so as to generate data-based indicia of an individual's overall health.

BACKGROUND OF THE INVENTION

A particular challenge in the fields of medicine and, indeed, healthcare generally is how to provide a quantitative assessment of an individual's overall health. Without some type of quantitative measurement, assessing the individual's current health and predicting his or her future health tends to varying degrees to be less precise. Conversely, a quantitative measurement of the individual's health can be useful to physicians and other healthcare providers in more rigorously evaluating the risks that an individual may yet develop a problematic medical condition in the future. Such a measurement, of course, is typically very helpful to insurance providers. Moreover, a quantitative measurement can convey to the individual himself or herself a more precise assessment of the individual's health condition, perhaps alerting the individual to change certain lifestyle or environmental variables so as to improve the individual's health.

Despite the benefits that a quantitative measurement of an individual's health can provide, conventional measurements tend to be limited to different, unrelated scores pertaining to distinct aspects of an individual's body and biological system. Accordingly, it is difficult to provide a total wellness assessment of an individual. Further, in the absence of such an overall assessments, it is also difficult to determine suggestions or incentives most likely to result in user decisions to make changes in lifestyle or environmental variables so as to improve the individual's health.

SUMMARY OF THE INVENTION

The present invention is directed to systems and methods for integrating health-relevant data from multiple sources and utilizing the integration to develop measurable indexes of an individual's wellness, or overall state of health. The systems and methods can incorporate and enhance statistically-valid sampling of various target populations. For those factors driven by lifestyle, individuals within these population groups can with continuous measurement, motivation and therapy potentially graduate to a higher health index.

One embodiment of the invention is a system for generating measurable indexes for providing a total wellness assessment or baseline for an individual. The system can include a data communications interface for accessing a plurality of databases of population data derived from samplings of one or more populations. Additionally, the baseline system can include an integration and synthesis engine for generating a plurality of weighting factors based upon a predetermined combination of the data, each weighting factor corresponding to a predetermined body region of the individual or to a predetermined health condition associated with the individual and based upon the population data. The system also can include a conditions-capture engine for capturing individual-specific data corresponding to a set of predetermined of health conditions associated with the individual. The system can further include a modeling tool for combining at least one of the plurality of weighting factors with the individual-specific data corresponding to a set of predetermined of health conditions associated with the individual. Moreover, the system can include a quotient generator for generating an individual-specific overall health score corresponding to the individual based on the combining of weighting factors, population data, and individual-specific data.

Another embodiment of the invention is a computer-implemented method for generating measurable indexes for providing a total wellness assessment of an individual. The method can include accessing a plurality of databases of population data derived from samplings of one or more populations; generating a plurality of weighting factors based upon a predetermined combination of the population data using a dynamic data integration and synthesis engine, each weighting factor corresponding to a predetermined body region of the individual or to a predetermined health condition associated with the individual and based upon the population data; and combining at least one of the plurality of weighting factors with individual-specific data corresponding to a set of predetermined of health conditions associated with the individual and based on the combining of weighting factors and individual-specific data computing an overall health score corresponding to the individual.

Still another embodiment of the invention are systems and methods for utilizing real time monitoring of the individual(s) for all or part of the weighting factors such that meaningful positive feedback to the individual alters lifestyle driven factors impacting wellness. For example, cessation of smoking, drug and alcohol use, excessive caloric intake, can be altered with behavior. Similarly, maintaining restrictions on type of diet in real time are effective for obesity and heart disease. In some cases, controlled dosing of self-dispensed medications such as insulin and medications for COPD and pain can be made more effective with real time monitoring and feedback. In such embodiments, an effective means of motivation toward the preferred lifestyle habits is for the individual(s) to be placed within short term or "episodic" groups, wherein the individuals with a group may share an affinity of improving lifestyle and can be motivated to aspire to membership in more advanced "social" groups. Indeed, care plans for incremental migration through a series of such social groups can be defined as networks (Episodic Social Networks/ESNs) linking these groups—especially when multiple behaviors are to be modified. The individual may not see the complexity of the network guiding them and may only feel the social forces designed to incrementally graduate them to a better lifestyle and better wellness assessment.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

The invention is directed to systems and methods for synthesizing and integrating health-relevant data. One aspect of the invention is a system and related methods that synthesize and integrate such data so as to generate measurable indexes that, in context, provide more statistically valid samplings of population data and synthesize the data with individual- or patient-specific data to generate a total wellness assessment of an individual, including an evidence-based holistic measurement of an individual's health.

Figure 1:
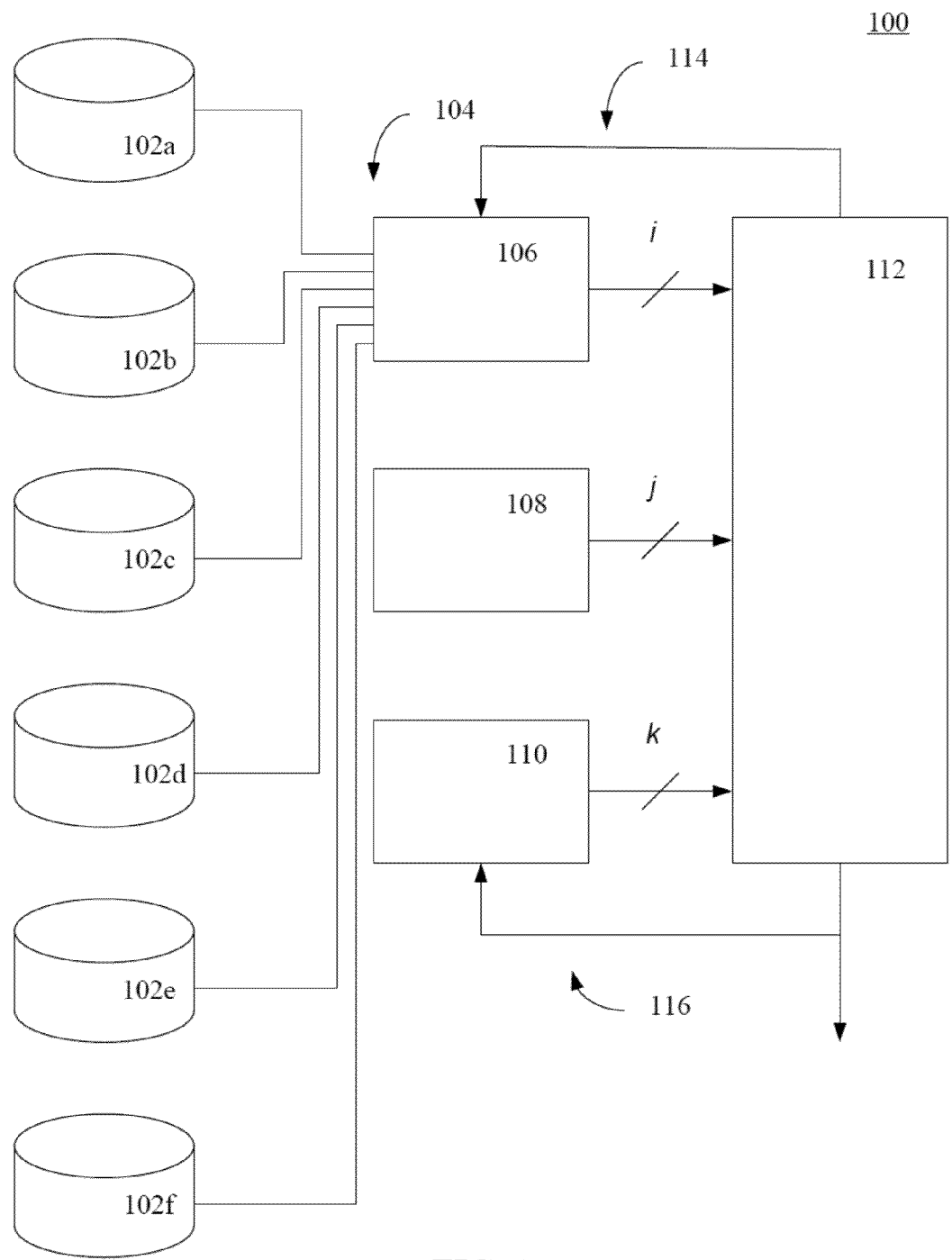
FIG. 1 is a schematic view of system for generating a total wellness assessment of an individual, according to one embodiment of the invention.

Referring initially to FIG. 1, a system 100 for generating measurable indexes for providing a total wellness assessment of an individual, according to one embodiment of the invention, is schematically illustrated. The system 100 illustratively includes a plurality of databases 202. Although an exemplary six databases 102a-f are shown, it will be readily apparent to one of ordinary skill based on the description herein that a different number of databases can be employed, be that number greater than or less than six.

The system 100 further illustratively includes a data communications interface 104. As shown, the interface 104 communicatively links each of the databases 102a-f with another element of the system 100. This element is termed an integration and synthesis engine 106, the operative features of which are described more particularly below. Additionally the system illustratively includes a conditions capture engine 108 and a modeling tool 110. Both the conditions capture engine 108 and the modeling tool 110 are communicatively linked to a quotient generator 112. The integration and synthesis engine likewise is communicatively linked to the quotient generator.

The databases 102a-f can communicatively link to the integration and synthesis engine 106 through the data communications interface 104 directly, as illustrated. In an alternate embodiment, however, the databases 102a-f can communicatively link to the integration and synthesis engine 106 through a data communications network (not explicitly shown). The network can be a local-area network (LAN), wide-area network (WAN), or the Internet. Thus, in any of these alternative embodiments the data communications interface 104 can be appropriately configured to communicatively link to one or more such data communications network.

One or more of the integration and synthesis engine 106, conditions capture engine 108, the modeling tool 110, and quotient generator 112 can be implemented in hardwired, dedicated circuitry for performing the operative functions described herein. Alternatively, however, one or more of these elements of the system 100 can be implemented in computer-readable code. Accordingly, the integration and synthesis engine 106, conditions capture engine 108, the modeling tool 110, and/or quotient generator 112 can be implemented in computer-readable code configured to execute on a general-purpose or application-specific computing device. In still another embodiment, however, one or more of these system elements can be implemented in a combination of hardwired circuitry and computer-readable code.

Operatively, the data communications interface 104 accesses the plurality of databases 102a-f. The different databases 102a-f store population data derived from samplings of one or more populations. As already noted, the number of databases of the system 100 can vary. Accordingly, the depth and breadth of the population data also can vary accordingly. The databases provide statistically valid samples of respective populations, as will be readily understood by one of ordinary skill in the art.

For example, the databases 102a-f can include demographic data, including regional statistics, job types, gender-relevant data, age-relevant data, environmental conditions, and any of a host of other data pertinent to assessing the health of representatives of the corresponding population. Additionally, the databases 102a-f can include an historical information database, which provides a timeline of information for tracing health statistics, such as the origins and trends of diseases, relevant treatments and medicines. Such data can include or be correlated with environmental and demographic groupings to disclose interactions between health of a population and environmental and/or demographic factors. The databases 102a-f also can include an actuarial database, which integrates insurance-related information such as risk probabilities and statistical assessments. Another of the databases 102a-f can be a medical database containing medical information extracted from a variety of sources pertaining to diseases, treatments, forms of "best practices" for health, and other medical information. The databases 102a-f also can include a genomic database that perhaps provides the most enhanced insight into the functioning of the human body; it can provide context linking genetic code to various physical, environmental, and behavioral factors of the representative population. Accordingly, this later database can provide insights into conditions and treatments in a dynamic and predictive manner.

Operatively, the integration and synthesis engine 106 generates a plurality of weighting factors based upon a predetermined combination of the population data, each weighting factor corresponding to a predetermined body region of the individual or to a predetermined health condition associated with the individual and based upon the population data. As illustrated, a variable number of data inputs can be supplied through the data communications interface 104 from the databases 102a-f to the integration and synthesis engine 106. Representative of such data is data relevant to age, sex, weight, blood pressure, cholesterol, smoking, job and profession, blood sugar, geography, and environmental factors, all of which can be used to derive the weighting factors based upon valid statistical techniques. The statistics can be based on relevant and emerging diseases, which one can monitor and which are modeled in the context of specific individuals as described herein. Similarly, established and measurable treatments can be factored into the model in order to determine direct health implications of these various factors.

The integration and synthesis engine 106 can be configured to compute and synthesize the disparate information drawn from the databases 102a-f. The integration and synthesis engine 106 thus can combine information from various sources with different perspectives and assign weighting factors to different health and biological elements. In this way health trends can be more readily discerned. For example, identifying an increasing prevalence of diabetes can indicate that a person's weight is a more significant factor, on average, than the person's cholesterol level in predicting long-term health of the individual. These weighting factors can be graduated by the integration and synthesis engine 106.

The conditions capture engine 108 operatively functions by capturing individual-specific data corresponding to a set of predetermined of health conditions associated with the individual. More particularly, the conditions capture engine 108 can capture current, historical, and genomic information pertaining to a specific individual and overlay the information with relevant weighting factors generated by the integration and synthesis engine 106.

At this point, the modeling tool 110 is configured to combine one or more of the plurality of weighting factors with the individual-specific data corresponding to a set of predetermined health conditions associated with the individual. The modeling tool projects or forecasts the impact that certain aspects of the individual body condition, behavioral attributes, environment, or other individual specific factors has on the individual's overall health score. For example, a person with a good diet and exercise regime may yet exhibit high levels of cholesterol. The individual's genomic profile and historical information may highlight this as a genetic trait. Accordingly, a stricter diet and more exercise is likely to have only minimal effect in reducing the individual's level of cholesterol, but targeted medications may provide immediate benefits.

Operatively, the quotient generator 112 generates an individual-specific overall health score corresponding to the individual based on the combining of weighting factors, population data, and individual-specific data. That is, the quotient generator 112 combines i units of information generated by the integration and synthesis engine 106 with j units of information generated by the conditions capture engine 108 and with k units of information generated by the modeling tool 110. By synthesizing the disparate data, the system 100 is able to create a numerical value of the individual's health.

For example, population data derived from the databases 102a-f can include data corresponding to the variables AGE, SEX, WEIGHT, BLOOD PRESSURE, and CHOLESTEROL, that is supplied by the integration and synthesis engine 106 to the quotient generator 112. The data can be overlaid with individual-specific data of 55 YEARS, MALE, 120 LBS., 130/90, and 234, corresponding to each of the exemplary population variables, which is supplied by the conditions capture engine 108. The modeling tool 110 can model various types of information so as to add new variables or data for projecting how an individual's health score would be altered by changes in health, behavioral, and/or environmental conditions. As already described, the quotient generator 112 can synthesize this disparate data to generate an overall wellness score for the individual.

Optionally, the system 100 can include one or more feedback mechanisms 114, 116. Accordingly, the system 100 is able to implement a dynamic model that can be refined based on various learning system principles, such as neural networks, machine learning, and the like. The system 100, accordingly, can be characterized as a closed-loop system.

The following statistical calculations can be employed. A first equation provides one population measure of wellness, termed here a quantum quotient, Q:

$$Q = \sum_{i=0}^{n} \frac{[(f_{1i} \cdot x_{1i}) + (f_{2i} \cdot x_{2i}) \ldots (f_{mi} \cdot x_{mi})]}{n},$$

where $f_{ji}$ is a weighting factor of individual i-th and the j-th of the m factors, which can include, for example, the following health-related factors: age, sex, weight, blood pressure, and blood sugar level for the i-th individual. For an individual, a quantum quotient, Q can similarly be computed:

$$Q = \frac{(f_1 \cdot x_1) + (f_2 \cdot x_2) \ldots (f_m \cdot x_m)}{m},$$

where, again, $f_j$ is a weighting factor applied to the j-th of the m factors, which can also include, for example, age, sex, weight, blood pressure, and blood sugar level. With an additional equation, positive or negative deviations can be factored against an established norm to create statistically-valid integrated scores:

$$Q' = \sum_{i=0}^{n} \frac{[(f_{1i} \cdot x_{1i} \pm \mu_{1i}) + (f_{2i} \cdot x_{2i} \pm \mu_{2i}) \ldots (f_{mi} \cdot x_{mi} \pm \mu_{mi})]}{n}.$$

Figure 2:
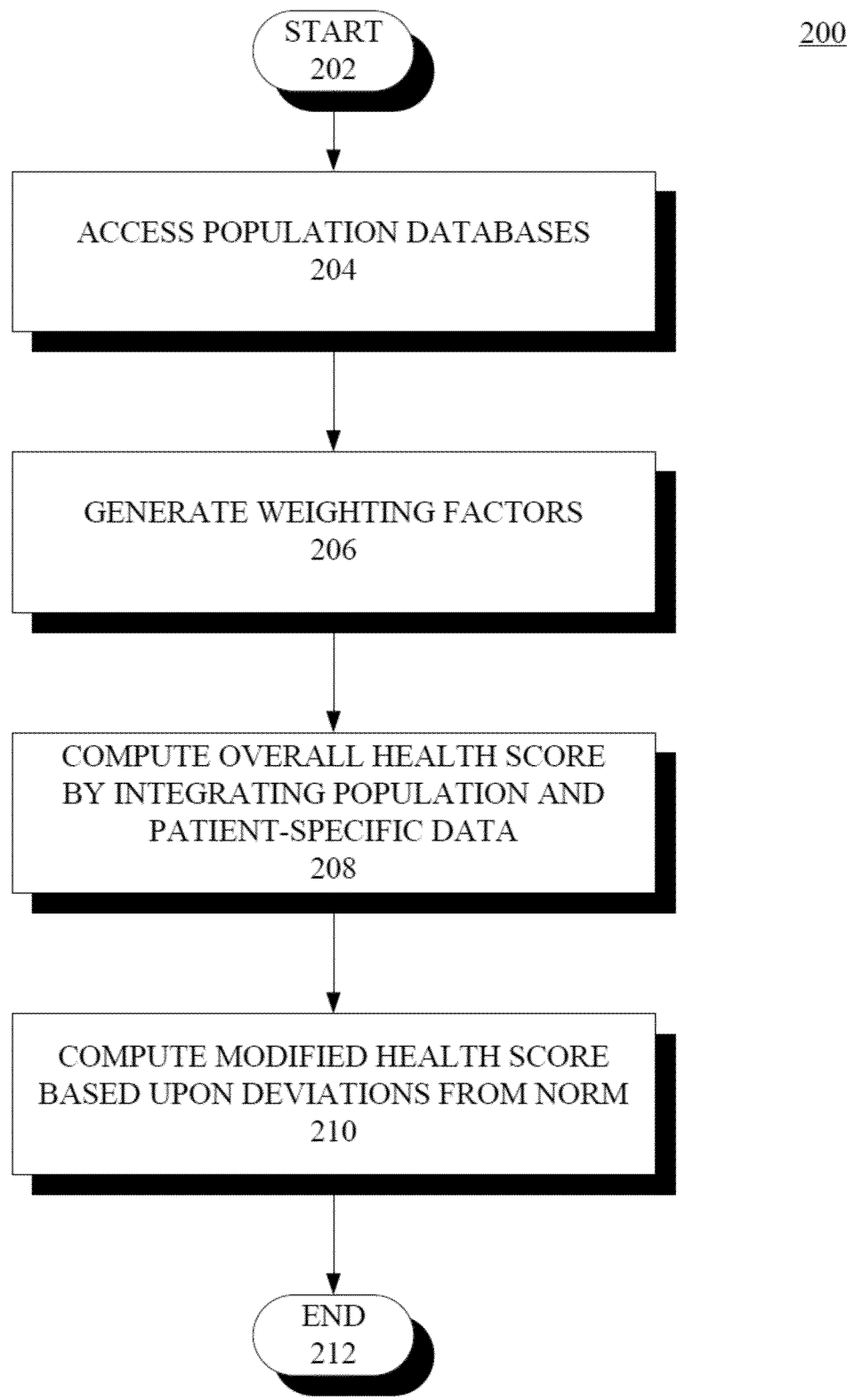
FIG. 2 is a flowchart of exemplary steps in a method for generating a total wellness assessment of an individual, according to another embodiment of the invention.

Referring now to FIG. 2, a flowchart is provided that illustrates certain method aspects of the invention. The flowchart depicts exemplary steps of a method 200 for generating measurable indexes for providing a total wellness assessment of an individual, according to another embodiment of the invention. The method illustratively includes, after the initial step 202, accessing a plurality of databases of population data derived from samplings of one or more populations at step 204. The method 200 additionally includes generating at step 206 a plurality of weighting factors based upon a predetermined combination of the population data using a dynamic data integration and synthesis engine. Each weighting factor, more particularly, corresponds to a predetermined body region of the individual or to a predetermined health condition associated with the individual and based upon the population data. The method 200 also includes combining at least one of the plurality of weighting factors with individual-specific data corresponding to a set of predetermined of health conditions associated with the individual and, based on the combining of weighting factors and individual-specific data, computing an overall health score corresponding to the individual at step 208.

The method 200 optionally can also include computing an integrated overall health score, as shown by optional step 210. The integrated overall health score can be based upon at least one deviation between the overall health score and a statistical norm derived from population data contained in one or more of the plurality of databases. The method 200 illustratively concludes at step 212.

More particularly, computing the integrated overall health score can be based upon projected changes in predetermined health conditions associated with the individual. Computing the integrated overall health score can be based upon projected environmental changes affected the individual.

According to another embodiment, the method 200 can further include generating a list of recommendations for the individual based upon the projected changes. The list of recommendations, more particularly, can include a therapeutic regime for the individual, an environmental change, and/or a behavioral change.

The method 200, according to yet another embodiment, can include updating at least one of the weighting factors. The updating can be based upon a statistically estimated trend.

In particular embodiments, one or more of weighting factors can be individually addressed and by collecting data associated with the user or the user's activities in real time, or at least sampled frequently enough with respect to long term variations to approximate real time. For example, a device can be provided monitor the user and the user's activities by collecting appropriate data. The device can be configured to provide monitoring (i.e., collect data) specific to specific weighting factors, but the various embodiments are not limited in this regard. That is, the device can be configured to collect data associated with the user and user activities not associated with factors. Thus, this additional data may allow the factors to be expanded over time.

Figure 3:
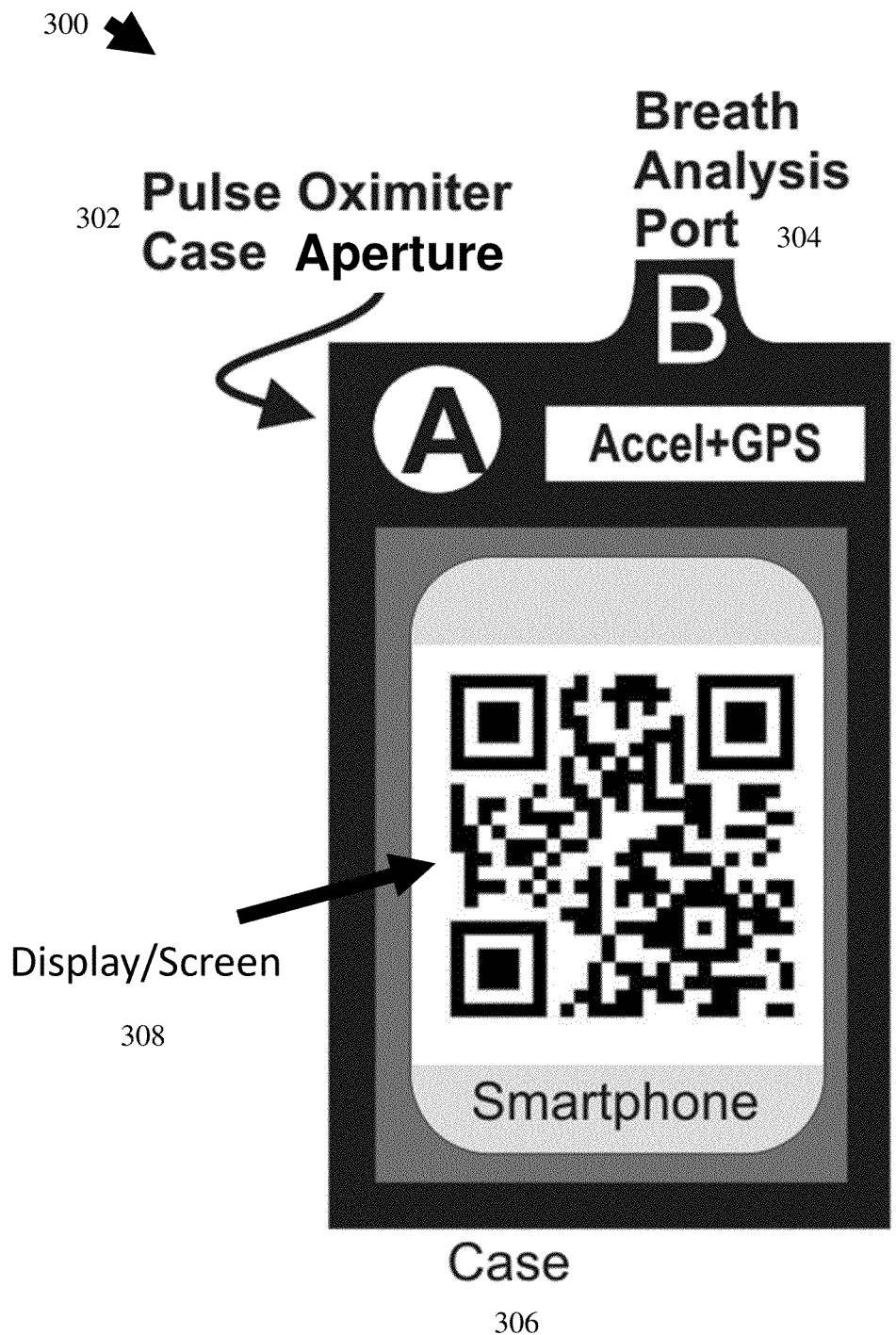
FIG. 3 is an example of real-time monitoring connected via a modified smartphone device.

An exemplary device 300 for carrying out one or more aspects of the various embodiments is shown in FIG. 3. FIG. 3 shows a smart-phone device configured to include software and hardware to record and relay measurements of pulse, oxygenation (via aperture 302), $CO_2$ content in breath (via sensor port 304), and acceleration, position and even mass of the individual (via sensors in case 306). However, the various embodiments are not limited to the data sets above and more or less datasets than described above. In some embodiments, the device can include sensors for measurements of the above-mentioned data sets or link to embedded sensors and ID parameters within the individual. It is conceivable that the entire data collection process could be contained in such an implantable device or personal article such that the individual becomes a connectable source of data, perhaps configured as a website, whenever they are in a field where wireless connectivity is available. However, in other embodiments, the smart-phone device can be configured to communicate with other devices to record and relay such datasets. For example, for measuring the mass of an individual, the smart-phone can include a strain gauge or other sensor for measuring mass or weight. Alternatively, the smart-phone can be configured to communicate, via a wireless or wireline connection, with a scale to collect such data. Similarly, other types of data can be collected using local or remote sensor devices.

As discussed in further detail below, the various embodiments of the invention provide for incentivizing particular decisions regarding lifestyle and environment. That is, based on particular decisions or reaching particular goals, the user can receive a reward or other incentive to maintain the lifestyle resulting from particular decisions.

In one particular embodiment, the device of FIG. 3 can be configured to display 308 a redeemable reward code (RRC) that represents stored achievement credits. These credits can be used to provide discounts or value towards goods and services for one or more particular vendors. The smartphone may autonomously accumulate such rewards. However, the various embodiments are not limited in this regard. That is, the rewards can be also made available via email, SMS messages, or any other means of communication at the device or another device associated with the user.

Although the foregoing description is directed primarily to a device operating autonomously to collect data and determine which incentives to provide, the various embodiments are not limited in this regard. Rather, the device can operate in conjunction with a server or other system, such as that of FIG. 1, to manage data collection and rewards for multiple users. Further, FIG. 3 shows just one exemplary configuration for a device in accordance with the various embodiments. In other embodiments, such a device can have more or less components than shown in FIG. 3.

As noted above, one aspect of the system and method illustrated above is that recommendations can be generated based upon projections of changes in an individual's lifestyle and environment. Specifically, desirable changes in an individual's lifestyle and environment. One option is to simply suggest that an individual cease participating in particular activities or cease engaging in activities in particular environments, i.e., a "cold turkey" approach and provide awards according. However, performing drastic changes can be difficult or even impossible for some individuals. Rather, for at least some individuals, it is better to alter the lifestyle and environment of the individual via a set of smaller incremental changes. Thus, once the set of smaller changes is completed, the individual has completed the necessary change in lifestyle or environment needed for improving his overall heath score. One exemplary recommendation plan is illustrated with respect to FIG. 4.

Figure 4:
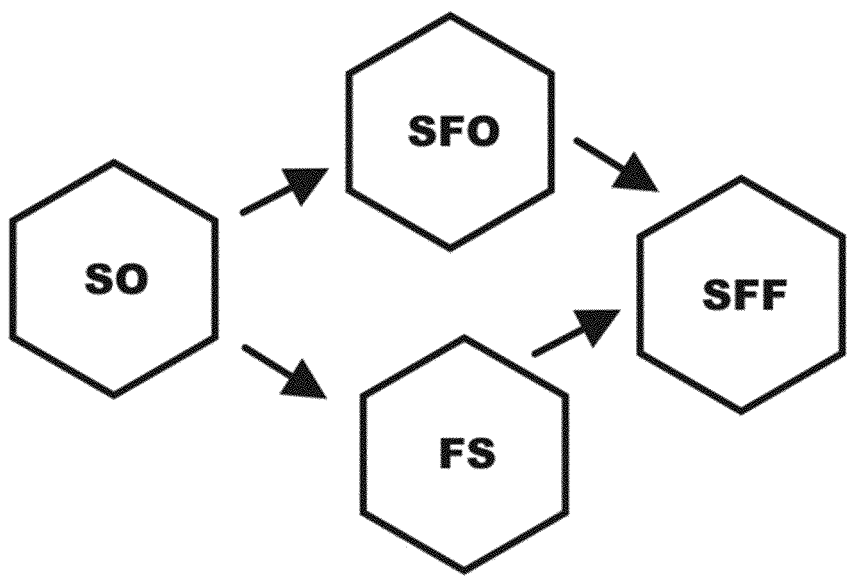
FIG. 4 is a network of episodic lifestyle steps in a wellness improvement care plan.

FIG. 4 shows a general care plan to move an individual from smoking and obese (SO) group or state to a smoke-free and fit (SFF) group or state. In a typical scenario, a physician would recommend that the individual cease smoking and concurrent reduce weight or improve fitness. However, achieving both goals simultaneously can be difficult for various reasons. In the various embodiments, the goals for improving the overall health score are achieved by dividing the overall goal into smaller goals and guiding the individual through smaller goals.

In a basic example, as shown in FIG. 4, the individual can be guided to from the SO state to the SFF state by way of going from the SO state to a state or group of smoking free-obese (SFO) and thereafter going to the SFF state. Alternatively, the individual can be guided from the SO state to a Fit-Smoking (FS) state or group and thereafter going to the SFF state. Thus, rather than dealing with the huge steps that the individual(s) may not see as practical, the transition from SO to SFF state can be taken as a series of small steps. Each of smaller steps can be incentivized, as described above. For example, a first reward can be provided for cessation of smoking, followed by a second reward when weight loss or physical fitness goals are reached.

As noted above, achieving an overall goal can be difficult. Moreover, achieving smaller goals can also be difficult. Accordingly, each of the smaller steps can be designed to enhance chances or opportunities of success. For example, in the case of FIG. 4, to transition the individual from the SO to the FS state, an incentive can be provided in the form a discount to a gym or fitness class. Further, the gym or fitness class can be selected such that it includes other individuals attempting to also transition from the SO to the FS state. Accordingly, these like-minded individuals can be directed to activities that will increase the likelihood of meeting each other and providing support to each other during the transition. That is, such individuals therefore form an episodic social network (ESN), as described in International Patent Application No. PCT/US 12/52,404, filed Aug. 25, 2012, and thus provides each other a social network or group that facilitates the chance that the individuals in the SO ESN will transition successfully to an FS ESN or state. Further, since the behavior of persons in such ESNs can be modeled a priori, the chances of success can be further enhanced by designing the incentives based on such modeling. That is, the past performance of individuals in the SO ESN can be used to determine how to best guide person to the FS ESN or state. A similar selection of incentives can be provided for other transitions.

In some embodiments, the partners offering the necessary incentives can be randomly selected. However, in other embodiments the partners providing the various incentives can also be selected for purposes of achieve a particular goal, including social or economic goals. For example, in the case of providing incentives to a gym membership or fitness classes, the partners can be associated with the entity designing the program. That is, a physician or hospital designing the program for the individual can select that the incentives come from affiliated fitness facilities or even a fitness facility managed by the physician or the hospital. Thus, not only is the individual being incentivized, but the incentives can be financially advantageous to the physician or hospital. Further, in the case of such related facilities, there may be a greater degree of sharing of information between the entities that will allow the fitness program for the individual to be tailored or otherwise be more effective in allowing the individual reaching his goals. For example, if the fitness facility has access to health information for the individual and has knowledge of particular medical issues for the individual, the individual can be provided fitness options geared towards addressing such issues. Further, the individual can be diverted from engaging in fitness activities that might be hazardous in view of his medical issues.

Although FIG. 4 illustrates only a few states or groups, the various embodiments are not limited in this regard. That is, any process, including that shown in FIG. 4, can be broken up into any number of states or groups. For example, the transition from SO to FS can include one or more intermediate states or groups, each also associated with an incentive. Such additional steps are illustrated with respect to FIG. 5.

Figure 5:
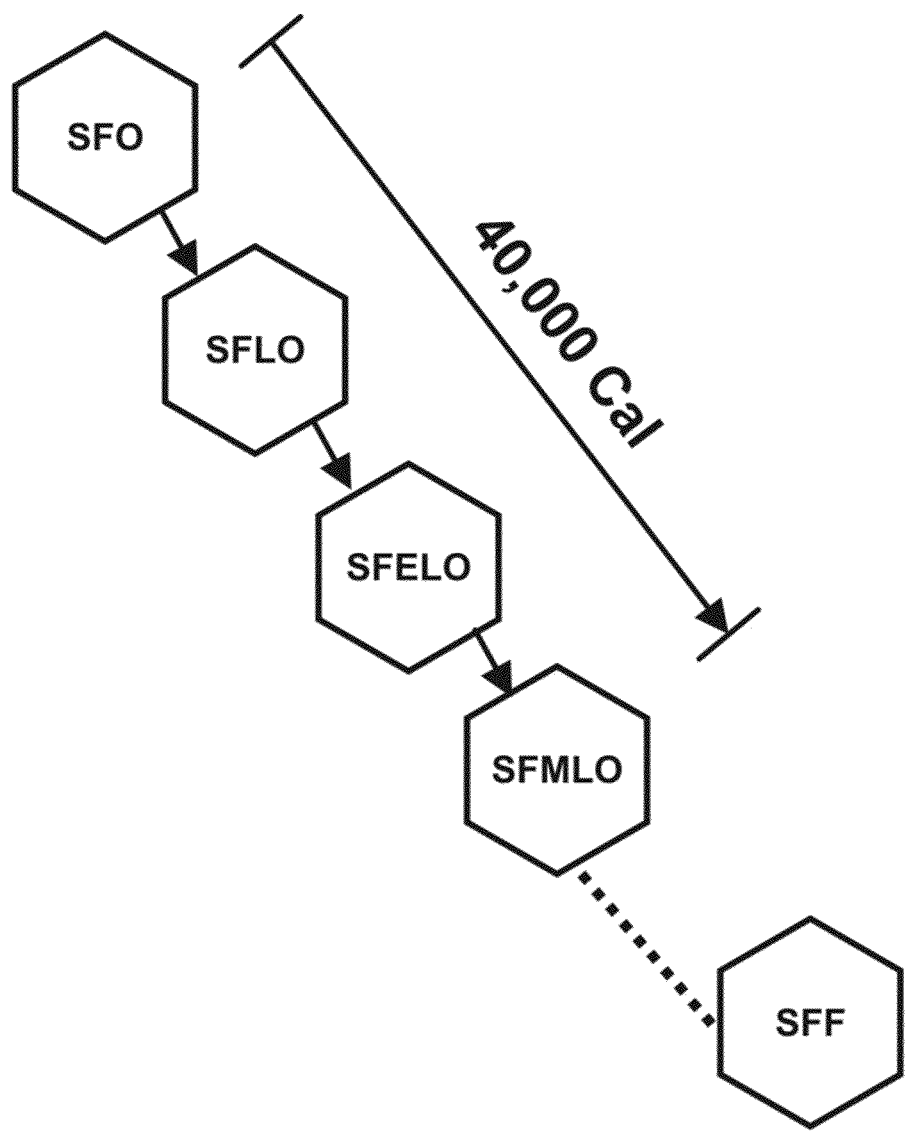
FIG. 5 is an example of an ESN incentive branch, inducing a positive decision.

FIG. 5 shows an exemplary set of states, groups, or ESNs for transitioning between the SFO and SFF ESNs of FIG. 4. In particular, these states, groups, or ESNs, and associated incentive, are associated with the objective to remove weight, defined as accumulated calories. In this example a deficit of approximately 3500 calories per week will equals a weight loss of 1 pound. Thus to lose 50 pounds, over the course of a year, this deficit would need to be consistently maintained for an overall deficit of 175,000 calories, A temporary major goal might be to first reach a deficit of 40,000 calories to target a 12 pound loss (or other amount), perhaps on the way to losing the 50 pounds. Additionally, a micro-goal of 3 pounds, 1 pound, or even ½ pound can also be provided. Each goal can be incentivized based on the type of goal. For example, small deficits in calories can be incentivized with small rewards in exchange for the sacrifice of denial. Thus a micro-goal of 3 pounds, 1 pound, or even ½ pound might be incentivized by providing a small spendable credit or other reward to the user. A major goal might be incentivized by more valuable rewards.

With respect to micro-goals, the various embodiments provide for visualization. For example, the accelerometer can detect that the known mass of the individual has done work by callisthenic movement, potentially prompted by the device, and offer a reward for the activity (i.e., the deficit). Similarly, a GPS device might calculate a gross movement while running and the pulse, oxygenation and $CO_2$ level integrated to imply exertion and metabolic achievement. Thus, based on such measurements, the attainment of the micro-goal can be detected and a reward can be provided. For example, a device, such as that of FIG. 4, can have a display or screen that might prompt: "You have achieved a micro-goal and are due a reward. You may spend the reward, accumulate it, or use it to offset expense. You may show the reward code at "XYZ health eats" for a calorie smart meal, or you may have a smaller less healthy treat that will not totally offset your caloric savings, or you may enjoy 1% off your personal healthcare insurance for this month (potentially saving 30% in one month)." Disregarding the economics which may require subscription subsidy from the individual, his employer, a medical care plan, insurance payer, etc., the individual is presented with what appears to be a free choice decision and an immediate reward. Thus behavior modification is provided via these micro-goals. Similarly, higher value rewards can be provided when a major goal is reached.

One advantage of the various embodiments is that since goals are monitored and messages are delivered direct to the user, there is no loss of privacy or embarrassment. For example, it avoids the need for an individual to publically admit or acknowledge a weight gain. Further, the individual can also see that they have made progress on the display. Instead of the public humiliation, the result of the weight gain can be loss of a potential reward. Further, in some cases, where a failure might be expected, a smaller reward to encourage the change in behavior can be provided. Alternatively, an incentive can be provided to encourage the user to engage in activities or take actions to overcome the deficit or failure.

An additional advantage of the various embodiments is that the micro-goals and major goals can be adjusted dynamically to account for various circumstances. For example, if healthy weight loss is being promoted, the value of the incentives may be reduced if weight loss occurs too quickly. On the other hand, if weight loss is occurring to slowly, higher value incentives can be provided to motivate the individual to continue the plan. Additionally, as discussed above with respect to FIG. 4, the incentives can be selected to incentivize the individual to proceed along a particular set of ESNs.

Such episodic plans may be quite detailed and complex and for given individuals with given health profiles and long term goals. Multiple goals may be combined in one care plan, weight loss, salt intake reduction, smoking cessation, and so on. The system may select and customize plans heuristically based on past experience with a given individuals or individuals who would have a similar profile.

In the case of autonomous monitoring, progress may be reported periodically via connectivity to the host system and integrated to adjust the individual(s) overall wellness assessment. This could include real time integration to Electronic Heath Records or other medical records platforms. Progress may be overseen by a payer who subsidizes the program or by a healthcare provider, and periodic feedback in the form of a report to the individual given. Perhaps most important, the individual may be coached, prompted, acknowledged by immediate human interaction as well as automated system prompts. In the event that medical intervention might be required (e.g., heart-rate exceeds recommended limits for age or condition), the individual can be alerted that intervention by a healthcare provided may be required. In the case where specialized attention is needed, the patient can be referred to the necessary specialists.

Some embodiments can be implemented via algorithms, methods, processes, and the like that predict and incent migration between affinity groups (as described in International Patent Application No. PCT/US12/52,404, filed Aug. 25, 2012) by detecting continuity and motivation by monotonically improving collected data and accelerating improvement could be defined. An individual committed to progress would exhibit a higher degree of continuous success and a higher rate of progress such that less than threshold entry into the next affinity group stage of the network could be permitted. Further, an individual who matches the progress of earlier successful individuals in wellness score and progress pattern could be accelerated. In the network, adaptive branching of ESN network plans based on individuals prior success and acceleration factors or correlation to prior successful network plans could justify acceleration.

Members of the next probable ESN affinity group in the sequence can become coaches as birds of a feather for aspiring individuals based on success prediction.

In another embodiment, the individual is implanted with their own identity server. All personal information, not just medical could be stored on it. The person's total experiences, acquired information, or predicted necessary information is on this internal wireless connected website manageable by them from the web.

The wireless connectivity would link them to other individuals in an ESN network or other proximity groups, or to opportunities, or to needs. The contents of the implantable device might drive a display or badge with identifying the individual and providing privileges, assets, requirements to be displayed as their contents and interpreted by machine intelligence. Identity would be established, doors would open as required (no locks), items acquired (stores without clerks), consequent economic transactions would occur, associations to other individuals made, directions given to sources of "satisfaction" all based on their needs, desires as accumulated over time in their "self" website.

In another embodiment, the wellness score, including dynamic scores, could be used to evaluate the specific or overall effectiveness of providers, physicians, therapists and procedures. The wellness sore could also rate the effectiveness of medications, durable medical equipment and therapies, either by individual, by group, or all prescribed individuals.

In still another embodiment, the weighted average can be dynamically adjustable by a profile calculated or stored from individuals with like health history or by any other type of grouping, e.g., a group of individuals currently in a same episode, a group of individuals associated with the same episodes, or a group of individuals with the same affinity or goals. Thus, the health scores are divided into groups (potentially affinity groups) of similar individuals. This second score can be used to indicate how hard an individual is trying to improve, given their background and compared to the rest of the population in the same group. In particular, it may show a greater propensity for failure or success with a given individual. Therefore, if a healthcare service implements a triage decision, this information may help adjust treatment to effect a most effective treatment. This can be especially important in the case of individuals with limited funds or having limited access to certain treatment. Such a score may also be used to adjust health insurance rates based on projected success or failure of treatment programs.

The exemplary embodiments discussed above have been presented solely for illustrative purposes and the various embodiments are not limited in this regard. Rather, the present disclosure contemplates that the various embodiments can be utilized in any scenario including any number and types of users and any number of resources.

Figure 6:
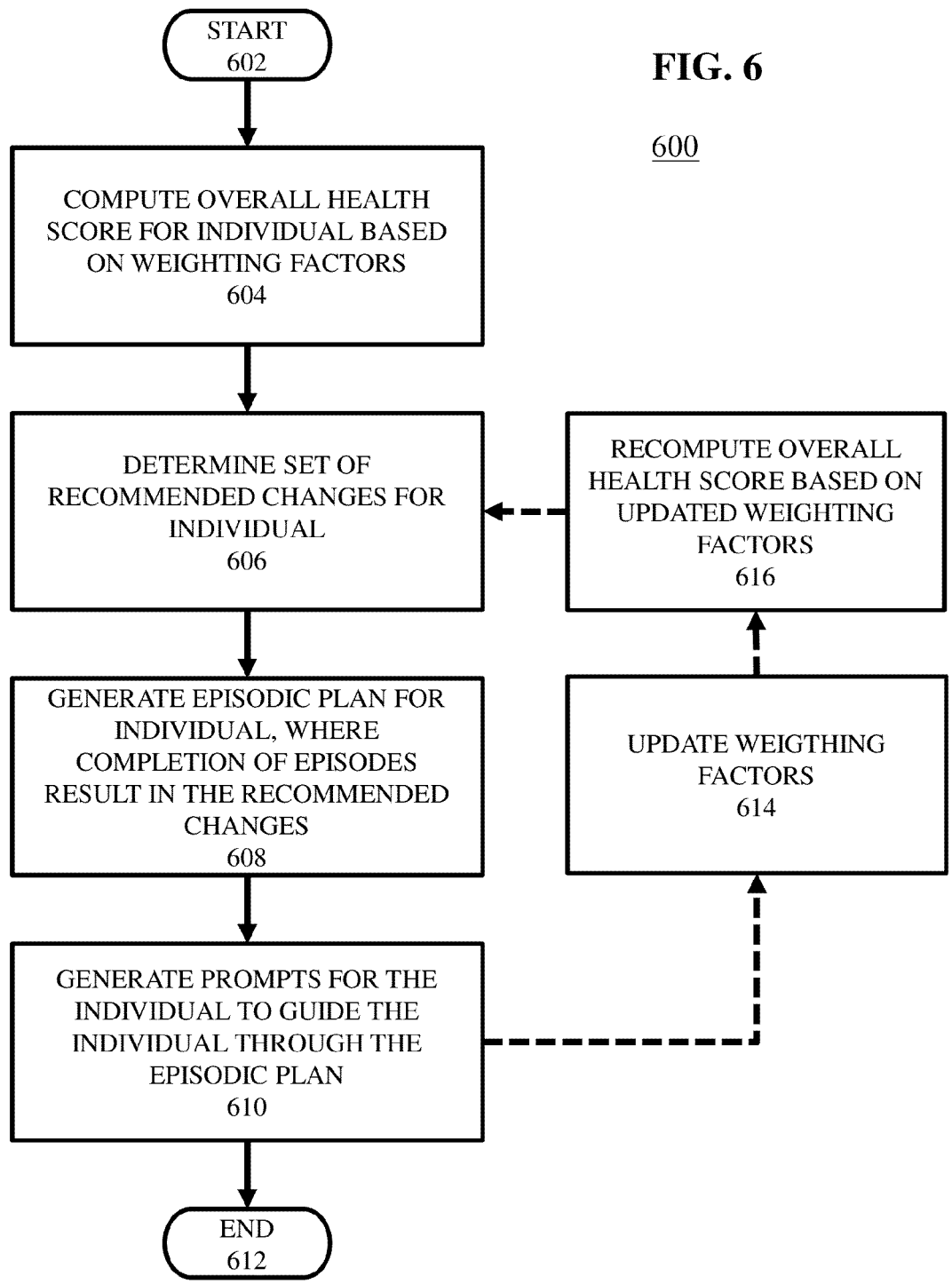
FIG. 6 is a flowchart of exemplary steps in a method according to another embodiment of the invention.

Now turning to FIG. 6, there is shown a flowchart of an exemplary method 600 in accordance with the various embodiments. The method 600 begins at step 602 and proceeds to step 604. At step 604, an overall health score for an individual can be computed based on weighting factors, as previously described above. Thereafter, at step 606, a set of recommend changes for the individual can be determined, again as previously discussed.

At step 608, an episodic plan can be generated for the individual. That is, a series of episodes or ESNs can be identified, such that when all the episodes are completed by the individual, the recommended changes of step 606 will have been effectuated. The episodic plan can be selected, as discussed above, into a series of episodes defining smaller goals for the individual to facilitate the recommended change. In some embodiments, the episodes can be associated with incentives to induce the individual to complete the goal associated with the episode. Further, the episodes can be associated with different a goal type. For example, major goals and minor goals. In such cases, the value of the incentives can vary based on the goal type.

At step 610, prompts for the individual can be generated to guide the individual through the episodic plan. The method can then end at step 612. The prompts can specify, as described above, rewards and other information to assist or induce the user to complete the goal associated with the episode.

As noted above, the prompts can be used to bring together individuals for support. Thus, the generating of the prompts can include identifying at least one other individual associated with another episodic plan include at least one episode from the series of episodes for the individual, determining whether the individual and the at least one other individual will be in the episode contemporaneously, and generating the prompts (i.e., the incentives) so that these individual interact. For example as described above, fellow former smokers in the SO state and transitioning to the FS state can be given an incentive to join a same gym or fitness class. Thus, they are more likely to meet and thus can provide support to each other while trying to get fit.

Alternatively, the prompts can be selected, as described above, to reach a second goal. For example, the incentives can be selected to cause the individual to perform activities associated with certain entities, such a facility associated with the individual's physician.

In some embodiments, as noted above, the series of episodes can be dynamically updated. For example, from step 610, the method can instead proceed to step 614. At step 614, the weighting factors can be updated. This can be accomplished by monitoring the heath of the individual as he proceeds through the episodes. Thereafter at step 616, the health scores can be recomputed based on the updated weighting factors. Finally, the episodic plan can be updated changed. For example, the method can proceed to step 606 to determine a set of changes, based now on the updated overall health score and a new episodic plan results at step 608. The new episodic plan can result in the adding of episodes to the original plan, the deletion of episodes, or the altering, adjusting, or replacement of episodes in the original plan. Thereafter, prompts can be generated as discussed above and further changes can be made as necessary.

Figure 7:
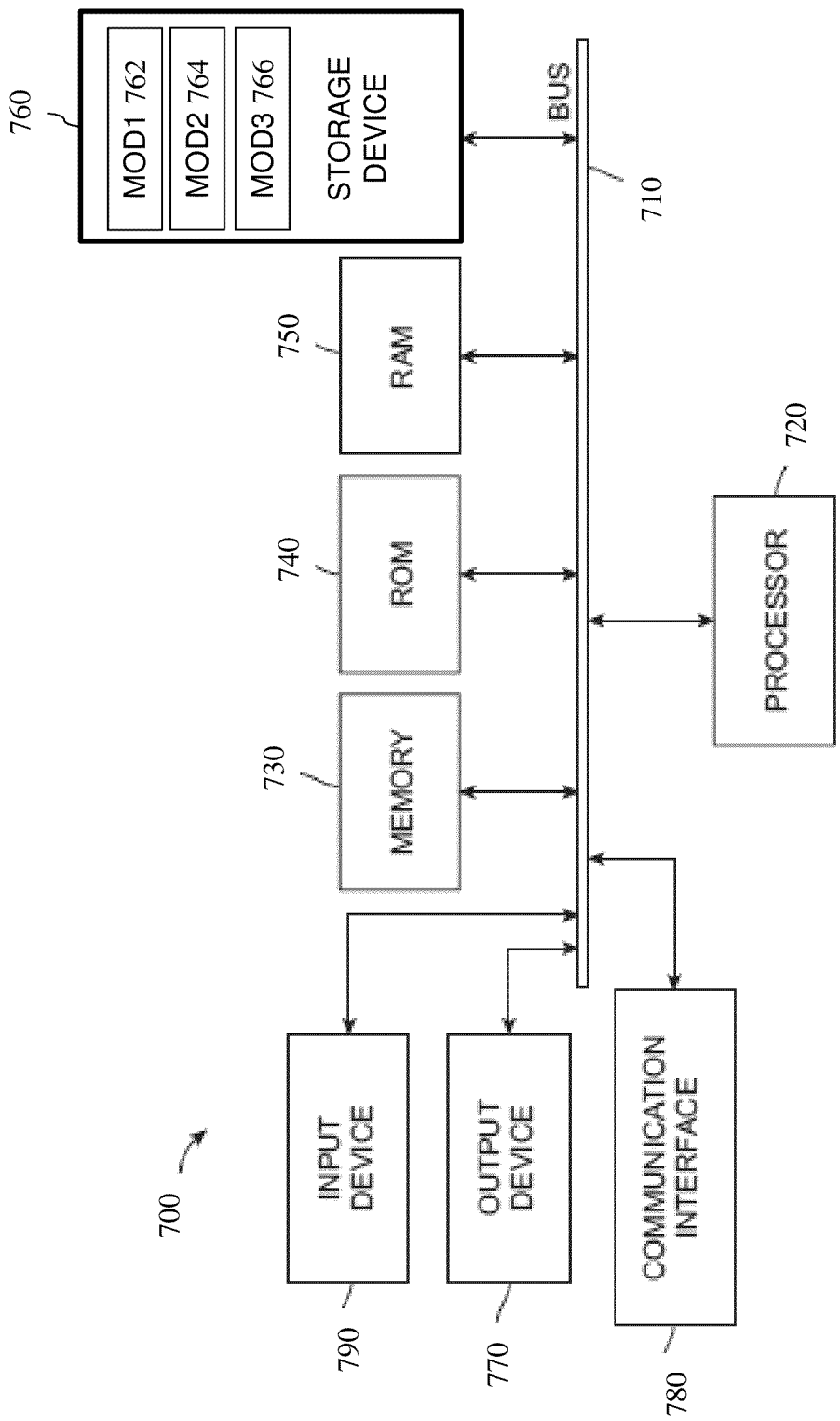
FIG. 7 illustrates an exemplary system for carrying out the various embodiments of the invention.

FIG. 7 illustrates an exemplary system 700 that can be used to carry out any of the various embodiments of the invention or the components of any portion of a system carrying the various embodiments of the invention. However, any portion of such a system can include more or less components than shown in FIG. 7. FIG. 7 defines a general-purpose computing device 700, including a processing unit (CPU or processor) 720 and a system bus 710 that couples various system components including the system memory 730, such as read only memory (ROM) 740, and random access memory (RAM) 750 to the processor 720. The system 700 can include a cache 722 of high speed memory connected directly with, in close proximity to, or integrated as part of the processor 720. The system 700 copies data from the memory 730 and/or the storage device 760 to the cache 722 for quick access by the processor 720. In this way, the cache 722 provides a performance boost that avoids processor 720 delays while waiting for data. These and other modules can control or be configured to control the processor 720 to perform various actions. Other system memory 730 may be available for use as well. The memory 730 can include multiple different types of memory with different performance characteristics. It can be appreciated that the disclosure may operate on a computing device 700 with more than one processor 720 or on a group or cluster of computing devices networked together to provide greater processing capability. The processor 720 can include any general purpose processor and a hardware module or software module, such as module 1 762, module 2 764, and module 3 766 stored in storage device 760, configured to control the processor 720 as well as a special-purpose processor where software instructions are incorporated into the actual processor design. The processor 720 may essentially be a completely self-contained computing system, containing multiple cores or processors, a bus, memory controller, cache, etc. A multi-core processor may be symmetric or asymmetric.

The system bus 710 may be any of several types of bus structures including a memory bus or memory controller, a peripheral bus, and a local bus using any of a variety of bus architectures. A basic input/output (BIOS) stored in ROM 740 or the like, may provide the basic routine that helps to transfer information between elements within the computing device 700, such as during start-up. The computing device 700 further includes storage devices 760 such as a hard disk drive, a magnetic disk drive, an optical disk drive, tape drive or the like. The storage device 760 can include software modules MOD1 762, MOD2 764, MOD3 766 for controlling the processor 720. Other hardware or software modules are contemplated. The storage device 760 is connected to the system bus 710 by a drive interface. The drives and the associated computer-readable storage media provide nonvolatile storage of computer readable instructions, data structures, program modules and other data for the computing device 700. In one aspect, a hardware module that performs a particular function includes the software component stored in a non-transitory computer-readable medium in connection with the necessary hardware components, such as the processor 720, bus 710, output device 770, and so forth, to carry out the function. The basic components are known to those of skill in the art and appropriate variations are contemplated depending on the type of device, such as whether the device 700 is a small, handheld computing device, a desktop computer, or a computer server.

Although the exemplary embodiment described herein employs a hard disk as storage device 760, it should be appreciated by those skilled in the art that other types of computer-readable media which can store data that are accessible by a computer, such as magnetic cassettes, flash memory cards, digital versatile disks, cartridges, random access memories (RAMs) 750, read only memory (ROM) 740, a cable or wireless signal containing a bit stream and the like, may also be used in the exemplary operating environment. Non-transitory computer-readable storag 1e media expressly exclude media such as energy, carrier signals, electromagnetic waves, and signals per se. However, non-transitory computer-readable storage media do include computer-readable storage media that store data only for short periods of time and/or only in the presence of power (e.g., register memory, processor cache, and Random Access Memory (RAM) devices).

To enable user interaction with the computing device 700, an input device 790 represents any number of input mechanisms, such as a microphone for speech, a touch-sensitive screen for gesture or graphical input, keyboard, mouse, motion input, speech and so forth. An output device 770 can also be one or more of a number of output mechanisms known to those of skill in the art. In some instances, multimodal systems enable a user to provide multiple types of input to communicate with the computing device 700. The communications interface 780 generally governs and manages the user input and system output. There is no restriction on operating on any particular hardware arrangement and therefore the basic features here may easily be substituted for improved hardware or firmware arrangements as they are developed.

For clarity of explanation, the illustrative system embodiment is presented as including individual functional blocks including functional blocks labeled as a "processor" or processor 720. The functions these blocks represent may be provided through the use of either shared or dedicated hardware, including, but not limited to, hardware capable of executing software and hardware, such as a processor 720, that is purpose-built to operate as an equivalent to software executing on a general purpose processor. For example, the functions of one or more processors presented in FIG. 7 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 740 for storing software performing the operations discussed below, and random access memory (RAM) 750 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 700 shown in FIG. 7 can practice all or part of the recited methods, can be a part of the recited systems, and/or can operate according to instructions in the recited non-transitory computer-readable storage media. Such logical operations can be implemented as modules configured to control the processor 720 to perform particular functions according to the programming of the module. For example, FIG. 7 illustrates three modules MOD1 762, MOD2 764 and MOD3 766, which are modules configured to control the processor 720. These modules may be stored on the storage device 760 and loaded into RAM 750 or memory 730 at runtime or may be stored as would be known in the art in other computer-readable memory locations.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

We claim:

1. A computer-implemented method for a providing wellness program for an individual, the method comprising:
   computing an overall health score corresponding to the individual based on a plurality of weighting factors, the weighting factors based at least on health conditions associated with the individual;
   determining one or more recommended goals for the individual based on the overall health score;
   obtaining a model identifying a plurality of episodes for a plurality of individuals associated with the recommended goals, a plurality of paths through the plurality of episodes, and criteria for classifying activities of the individual into one or more of the plurality of episodes, each of the plurality of episodes associated with a different set of finite temporal boundaries and non-temporal boundaries;
   generating an episodic plan for the individual based on the model, the episodic plan comprising a series of episodes for the individual from the plurality of episodes that when completed will result in the individual having implemented the recommended goals;
   generating a series of prompts for the individual, the series of prompts selected to guide the individual through the episodic plan using one or more of the plurality of paths;
   generating an episodic group in which to place the individual, the episodic group consisting of one or more other individuals presently assigned a same path between a same two or more adjacent episodes along their respective episodic plans; and as the individual completes paths associated with episodes in the episodic plan, migrating the individual to a second episodic group consisting at least partially of different individuals who are assigned to the subsequent path between updated adjacent episodes in their relative episodic plans.

2. The method of claim 1, where the generating of the series of prompts further comprises associating an incentive with a completion of at least one portion of the series of the episodes.

3. The method of claim 2, further comprising:
   designating each of the episodes as one of a major goal type and a micro-goal type, and
   selecting a value of the incentive based on a type of goal.

4. The method of claim 1, wherein the generating of the series of episodic group comprises:
   identifying at least one other individual associated with another episodic plan comprising at least one episode from the series of episodes;
   determining whether the at least one episode for the individual and the at least one other individual will occur contemporaneously; and
   in response to determining that the at least one episode will occur contemporaneously for the individual and the at least one other individual, selecting incentives for the individual and the at least one other individual to induce the individual and the at least one other individual to interact during the at least one episode.

5. The method of claim 1, wherein the generating of the series of prompts is performed by a first entity, and wherein the series of prompts for at least one of the series of episodes are selected to induce the individual to perform at least one activity associated with at least one of the series of episodes with a second entity affiliated with the first entity.

6. The method of claim 1, further comprising:
   updating the plurality of weighting factors after the completion of a portion of the series of episodes to yield an updated plurality of weighting factors;
   recomputing the overall health score based on the updated plurality of weighting factors to yield an undated health score; and
   adjusting the episodic plan for the individual based on the updated health score.

7. The method of claim 6, wherein the adjusting further comprises at least one of adding an episode to the series of episodes, removing an episode from the series of episodes, or altering an episode from the series of episodes.

8. A system for providing a wellness program for an individual, the system comprising:
   a processor;
   a computer-readable medium, having stored therein a plurality of instructions for causing the processor to perform steps comprising:
      computing an overall health score corresponding to the individual based on a plurality of weighting factors, the weighting factors based at least on health conditions associated with the individual;
      determining one or more recommended goals for the individual based on the overall health score;
      obtaining a model identifying a plurality of episodes for a plurality of individuals associated with the recommended goals, a plurality of paths through the plurality of episodes, and criteria for classifying activities of the individual into one or more of the plurality of episodes, each of the plurality of episodes associated with a different set of finite temporal boundaries and non-temporal boundaries;
      generating an episodic plan for the individual based on the model, the episodic plan comprising a series of episodes for the individual from the plurality of episodes that when completed will result in the individual having implemented the recommended goals; and
      generating a series of prompts for the individual, the series of prompts selected to guide the individual through the episodic plan using one or more of the plurality of paths;

generating an episodic group in which to place the individual, the episodic group consisting of one or more other individuals presently assigned a same path between a same two or more adjacent episodes along their respective episodic plans; and as the individual completes paths associated with episodes in the episodic plan, migrating the individual to a second episodic group consisting at least partially of different individuals who are assigned to the subsequent path between updated adjacent episodes in their relative episodic plans.

9. The system of claim 8, wherein the generating of the series of prompts further comprises associating an incentive with a completion of at least one portion of the series of the episodes.

10. The system of claim 9, the computer-readable medium further comprising instructions for causing the processor to perform steps comprising:
 designating each of the episodes as one of a major goal type and a micro-goal type, and
 selecting a value of the incentive based on a type of goal.

11. The system of claim 8, wherein the generating of the episodic group comprises:
 identifying at least one other individual associated with another episodic plan comprising at least one episode from the series of episodes;
 determining whether the at least one episode for the individual and the at least one other individual will occur contemporaneously; and
 in response to determining that the at least one episode will occur contemporaneously for the individual and the at least one other individual, selecting the incentives for the individual and the at least one other individual to induce the individual and the at least one other individual to interact during the at least one episode.

12. The system of claim 8, wherein the generating of the series of prompts is performed by a first entity, and wherein the series of prompts for at least one of the series of episodes are selected to induce the individual to perform at least one activity associated with at least one of the series of episodes with a second entity affiliated with the first entity.

13. The system of claim 8, the computer-readable medium further comprising instructions for causing the processor to perform steps comprising:
 updating the plurality of weighting factors after the completion of a portion of the series of episodes to yield an updated plurality of weighting factors;
 recomputing the overall health score based on the updated plurality of weighting factors to yield an undated health score; and
 adjusting the episodic plan for the individual based on the updated health score.

14. The system of claim 13, wherein the adjusting further comprises at least one of adding an episode to the series of episodes, removing an episode from the series of episodes, or altering an episode from the series of episodes.

15. A computer-readable storage medium, having stored thereon a plurality of instructions comprising code sections for performing a method comprising:
 computing an overall health score corresponding to the individual based on a plurality of weighting factors, the weighting factors based at least on health conditions associated with the individual;
 determining one or more recommended goals for the individual based on the overall health score;
 obtaining a model identifying a plurality of episodes for a plurality of individuals associated with the recommended goals, a plurality of paths through the plurality of episodes, and criteria for classifying activities of the individual into one or more of the plurality of episodes, each of the plurality of episodes associated with a different set of finite temporal boundaries and non-temporal boundaries;
 generating an episodic plan for the individual based on the model, the episodic plan comprising a series of episodes for the individual from the plurality of episodes that when completed will result in the individual having implemented the recommended goals;
 generating a series of prompts for the individual, the series of prompts selected to guide the individual through the episodic plan using one or more of the plurality of paths;
 generating an episodic group in which to place the individual, the episodic group consisting of one or more other individuals presently assigned a same path between a same two or more adjacent episodes along their respective episodic plans; and as the individual completes paths associated with episodes in the episodic plan, migrating the individual to a second episodic group consisting at least partially of different individuals who are assigned to the subsequent path between updated adjacent episodes in their relative episodic plans.

16. The computer-readable storage medium of claim 15, where the generating of the series of prompts further comprises associating an incentive with a completion of at least one portion of the series of the episodes.

17. The computer-readable storage medium of claim 16, the method further comprising:
 designating each of the episodes as one of a major goal type and a micro-goal type, and
 selecting a value of the incentive based on a type of goal.

18. The computer-readable storage medium of claim 15, wherein the generating of the episodic group comprises:
 identifying at least one other individual associated with another episodic plan comprising at least one episode from the series of episodes;
 determining whether the at least one episode for the individual and the at least one other individual will occur contemporaneously; and
 in response to determining that the at least one episode will occur contemporaneously for the individual and the at least one other individual, selecting the incentives for the individual and the at least one other individual to induce the individual and the at least one other individual to interact during the at least one episode.

19. The computer-readable storage medium of claim 15, wherein the generating of the series of prompts is performed based on inputs from a first entity, and wherein the series of prompts for at least one of the series of episodes are selected to induce the individual to perform at least one activity associated with at least one of the series of episodes with a second entity affiliated with the first entity.

20. The computer-readable storage medium of claim 15, the method further comprising:
 updating the plurality of weighting factors after the completion of a portion of the series of episodes to yield an updated plurality of weighting factors;
 recomputing the overall health score based on the updated plurality of weighting factors to yield an undated health score; and
 adjusting the episodic plan for the individual based on the updated health score.

* * * * *